(12) United States Patent
Hollis

(10) Patent No.: US 11,969,574 B2
(45) Date of Patent: Apr. 30, 2024

(54) WALL MOUNTED INSULIN CADDY

(71) Applicant: Andrew Hollis, Davison, MI (US)

(72) Inventor: Andrew Hollis, Davison, MI (US)

(*) Notice: Subject to any disclaimer, the term of this patent is extended or adjusted under 35 U.S.C. 154(b) by 18 days.

(21) Appl. No.: 17/947,578

(22) Filed: Sep. 19, 2022

(65) Prior Publication Data

US 2024/0100241 A1 Mar. 28, 2024

(51) Int. Cl.
*A61M 5/00* (2006.01)

(52) U.S. Cl.
CPC ....... *A61M 5/003* (2013.01); *A61M 2209/082* (2013.01)

(58) Field of Classification Search
CPC . A61M 5/003; A61M 5/008; A61M 2209/082
See application file for complete search history.

(56) References Cited

U.S. PATENT DOCUMENTS

| | | | | |
|---|---|---|---|---|
| 3,866,992 A * | 2/1975 | Katz | ................. | B43M 99/007 211/69.5 |
| 4,850,484 A * | 7/1989 | Denman | ............... | A61M 5/008 211/74 |
| D313,889 S * | 1/1991 | Gakhar | .......................... | D3/229 |
| 5,148,919 A * | 9/1992 | Rubin | ...................... | B01L 9/06 211/74 |
| 5,188,242 A * | 2/1993 | Smith | ..................... | B25F 5/029 248/205.3 |
| 5,232,103 A * | 8/1993 | Koenig | ................ | B43K 23/002 211/69.5 |
| 5,330,261 A * | 7/1994 | Bennett | ................. | A47F 3/0486 40/597 |
| 5,351,866 A | 10/1994 | Foss | | |
| 5,775,485 A | 7/1998 | Dierking | | |
| 5,950,832 A * | 9/1999 | Perlman | .................... | B01L 9/06 422/570 |
| D476,088 S * | 6/2003 | Wescott, III | ................. | D24/230 |
| D527,903 S * | 9/2006 | Chan | .............................. | D3/315 |
| 7,314,142 B2 * | 1/2008 | Lyman, Jr. | ........... | B43M 99/006 206/214 |
| 7,556,159 B2 * | 7/2009 | Robertson | .............. | A47B 96/02 211/75 |
| 7,611,012 B2 * | 11/2009 | Ross | ....................... | F25D 25/00 211/60.1 |

(Continued)

*Primary Examiner* — Patrick D Hawn
(74) *Attorney, Agent, or Firm* — Gregson IP Law LLC

(57) ABSTRACT

A wall-mounted insulin caddy according to the present invention includes a caddy body having a flat rear surface, an outer front surface, a pair of rounded corners, a top caddy body surface and a bottom caddy body surface, one or more removable adhesive strips coupled to the flat rear surface for mounting the caddy body to a wall and label on the outer front surface for identifying contents of any vials stored within the caddy body. The caddy body has a plurality of cylindrical storage locations, each of the plurality of cylindrical storage locations comprises a cavity within the caddy body accessible from a top caddy body surface for storing a vial, and a drainage hole from within the cylindrical storage locations through a bottom caddy surface. The caddy body reduces external light passing into vials placed within one of the plurality of cylindrical storage locations and each of the plurality of cylindrical storage locations has a chamfered vial slot opening for easier vial installation.

7 Claims, 4 Drawing Sheets

(56) References Cited

U.S. PATENT DOCUMENTS

| | | | | |
|---|---|---|---|---|
| 8,034,305 | B2 * | 10/2011 | LaFleur | G01N 35/025 211/74 |
| D664,769 | S * | 8/2012 | Kinskey | D3/315 |
| 8,789,713 | B2 * | 7/2014 | Koller | A47F 7/0028 211/74 |
| 8,827,075 | B2 * | 9/2014 | Seiwell | A61M 5/008 206/443 |
| 9,049,928 | B2 * | 6/2015 | Lesbirel | B65B 21/04 |
| D739,182 | S * | 9/2015 | Ryu | D7/602 |
| 9,402,785 | B1 | 8/2016 | Pazouki | |
| D793,088 | S * | 8/2017 | Ou | D3/315 |
| D805,870 | S * | 12/2017 | Kinskey | D8/71 |
| 9,969,208 | B1 * | 5/2018 | Hall | B43L 1/008 |
| 10,925,383 | B2 * | 2/2021 | Murakami | A45D 40/00 |
| D1,001,609 | S * | 10/2023 | Alles | D8/71 |
| 2007/0090070 | A1 * | 4/2007 | Langham | A61J 7/0069 211/74 |

* cited by examiner

WALL MOUNTED INSULIN CADDY

TECHNICAL FIELD

This application relates in general to an article of manufacture for providing drug storage devices, and more specifically, to an article of manufacture providing a wall-mounted insulin caddy.

BACKGROUND

Insulin storage is challenging. The vials cannot be out of the refrigerator or in direct sunlight. many people leave them in their bulky boxes and stack them in the door or on a shelf Current storage for insulin vials required refrigeration. Many people store their vials in the "butter compartment" on the door of their refrigerator. This takes up valuable space and can also expose unboxed vials to direct sunlight and varying temperatures when the door is opened. Also, commonly vials that are stored loosely in the butter compartment fall and break when the door is jerked open.

Therefore, a need exists for an article of manufacture for providing a wall-mounted insulin caddy. The present invention attempts to address the limitations and deficiencies in prior solutions according to the principles and example embodiments disclosed herein.

SUMMARY

In accordance with the present invention, the above and other problems are solved by providing an article of manufacture providing a wall-mounted insulin caddy according to the principles and example embodiments disclosed herein.

In one embodiment, the present invention is an article of manufacture for providing a wall-mounted insulin caddy. The wall-mounted insulin caddy includes a caddy body having a flat rear surface, an outer front surface, a pair of rounded corners, a top caddy body surface and a bottom caddy body surface, one or more removable adhesive strips coupled to the flat rear surface for mounting the caddy body to a wall, and may label on the outer front surface for identifying contents of any vials stored within the caddy body. The caddy body has a plurality of cylindrical storage locations, each of the plurality of cylindrical storage locations comprises a cavity within the caddy body accessible from a top caddy body surface for storing a vial, and a drainage hole from within the cylindrical storage locations through a bottom caddy surface. The caddy body reduces external light passing into vials placed within one of the plurality of cylindrical storage locations and each of the plurality of cylindrical storage locations has a chamfered vial slot opening for easier vial installation The foregoing has outlined rather broadly the features and technical advantages of the present invention in order that the detailed description of the invention that follows may be better understood. Additional features and advantages of the invention will be described hereinafter that form the subject of the claims of the invention.

It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Referring now to the drawings in which like reference numbers represent corresponding parts throughout.

DETAILED DESCRIPTION

Figure 1:
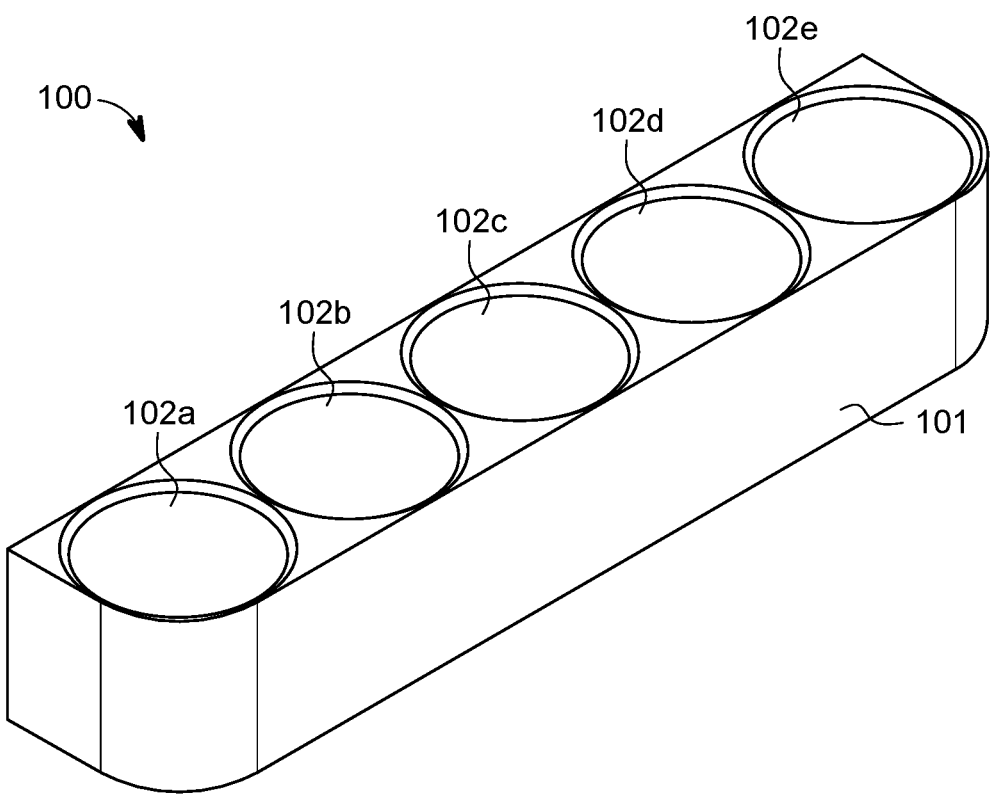
FIG. 1 illustrates an example embodiment of an article of manufacture providing a wall-mounted insulin caddy according to the present invention.

This application relates in general to an article of manufacture for providing drug storage devices, and more specifically, to an article of manufacture providing a wall-mounted insulin caddy according to the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In describing embodiments of the present invention, the following terminology will be used. The singular forms "a," "an," and "the" include plural referents unless the context clearly dictates otherwise. As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary. As used herein, the singular forms "a," "an," and "the" are intended to include the plural forms as well, unless the context clearly indicates otherwise.

It further will be understood that the terms "comprises," "comprising," "includes," and "including" specify the presence of stated features, steps, or components, but do not preclude the presence or addition of one or more other features, steps, or components. It also should be noted that in some alternative implementations, the functions and acts noted may occur out of the order noted in the figures. For example, two figures shown in succession may in fact be executed substantially concurrently or may sometimes be executed in the reverse order, depending upon the functionality and acts involved.

The terms "individual," and "user" refer to an entity, e.g., a human, using an article of manufacture providing a wall-mounted insulin caddy according to the present invention. The term user herein refers to one or more users.

The term "invention" or "present invention" refers to the invention being applied for via the patent application with the title "Wall-Mounted Insulin Caddy." The invention may be used interchangeably with caddy.

In general, the present disclosure relates to an article of manufacture providing a wall-mounted insulin caddy according to the present invention. To better understand the present invention, FIG. 1 illustrates an example embodiment of an article of manufacture providing a wall-mounted insulin caddy according to the present invention. A wall-mounted insulin caddy 100 that holds various numbers of vials (typically 5 but can be more or less). The caddy body 101 mounts to the side wall of the refrigerator with easily removable adhesive, for example, via 3M™ adhesive tape. The wall-mounted insulin caddy 100 creates an out-of-the-way place to store the insulin that prevents vials from falling on the floor. By storing on the wall, the butter compartment is open for normal use, and the exposure to direct sunlight is drastically reduced. While the preferred embodiment disclosed in the Figures describes a caddy with 5 storage locations 102a-e having a fixed size, one of ordinary skill in the art will readily recognize that any number of storage locations 102a-e may be included in the wall-mounted insulin caddy 100 with each of the storage locations 102a-e being sized to hold various sized vials. The example embodiments are disclosed for exemplary purposes that are not intended to limit the present invention. The wall-mounted insulin caddy 100 is defined within the limitations recited within the attached claims.

Figure 2:
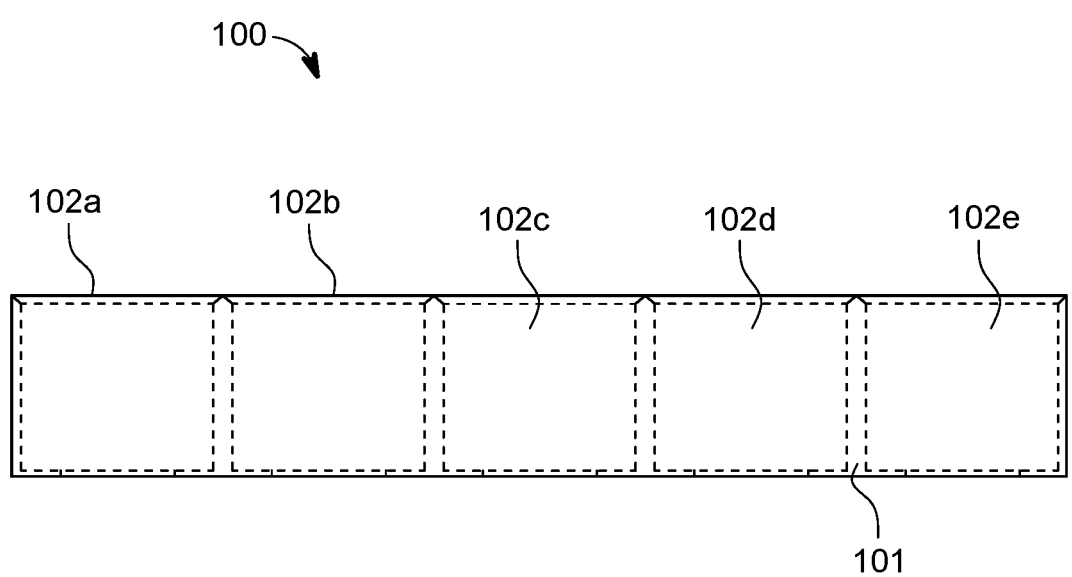
FIG. 2 illustrates a front view of an article of manufacture providing a wall-mounted insulin caddy according to the present invention.

FIG. 2 illustrates a front view of an article of manufacture providing a wall-mounted insulin caddy according to the present invention. The wall-mounted insulin caddy 100 shown in FIG. 2 illustrates a 5 storage location caddy 100 having equally sized storage locations 102a-e in the caddy body 101. In a preferred embodiment, each storage location 102a-e is 1" wide and 0.94" tall. The caddy body 101 is made of rigid plastic, such as Polylactic Acid (PLA), Polyethylene terephthalate glycol (PET(G)) or Acrylonitrile, Butadiene, Styrene (ABS), that does not expose the contents of the vials stored therein to light.

Figure 3:
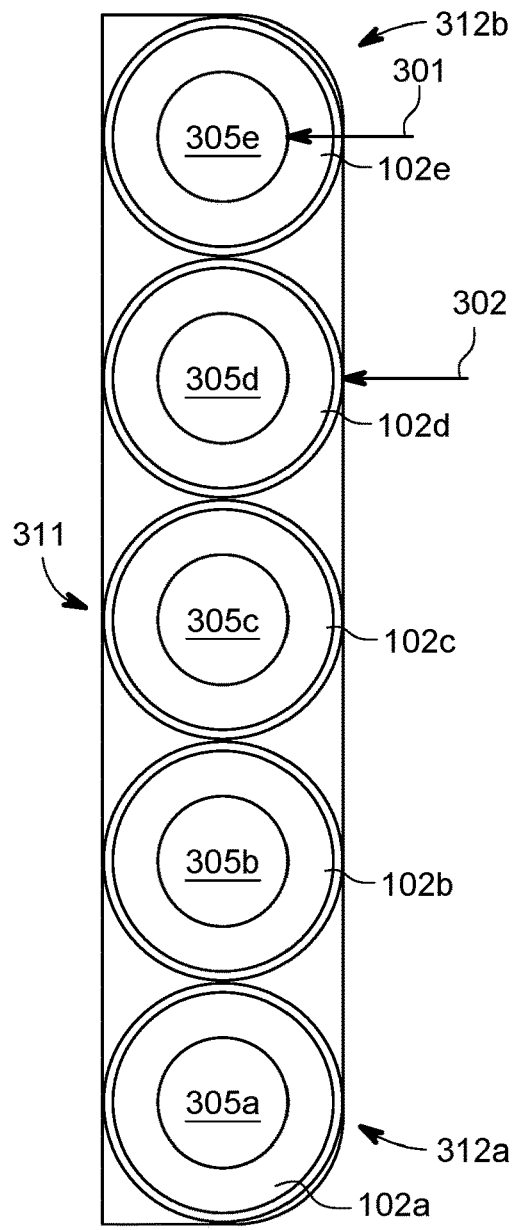
FIG. 3 illustrates a top view of an article of manufacture providing a wall-mounted insulin caddy according to the present invention.

FIG. 3 illustrates a top view of an article of manufacture providing a wall-mounted insulin caddy according to the present invention. The wall-mounted insulin caddy 100 shown in FIG. 2 illustrates a 5 storage location caddy 100 having each storage location 102a-e providing cylindrical cavities within the caddy body 101. Each of the storage locations 102a-e has a 0.59" drainage hole 305a-e through a bottom surface of the caddy body 101. Each storage location cavity 102a-e also has a chamfered vial slot opening for easier vial installation. The caddy body 101 also comprises a flat rear surface 311 and a pair of rounded front corners 312a-b.

Figure 4:
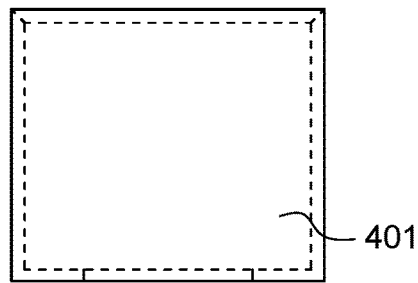
FIG. 4 illustrates an end view of an article of manufacture providing a wall-mounted insulin caddy according to the present invention.

FIG. 4 illustrates an end view of an article of manufacture providing a wall-mounted insulin caddy according to the present invention. The caddy body 101 is shown having an outside width of 1.10" with the 1" diameter storage location 102a-e centered therein. The wall thickness of the storage locations 102a-e in the caddy body 101 is configured to be strong enough to restrain and hold a vial. Other wall thicknesses may be utilized as needed depending upon the mass of the vial and insulin to be placed within the storage locations 102a-e.

Figure 5:
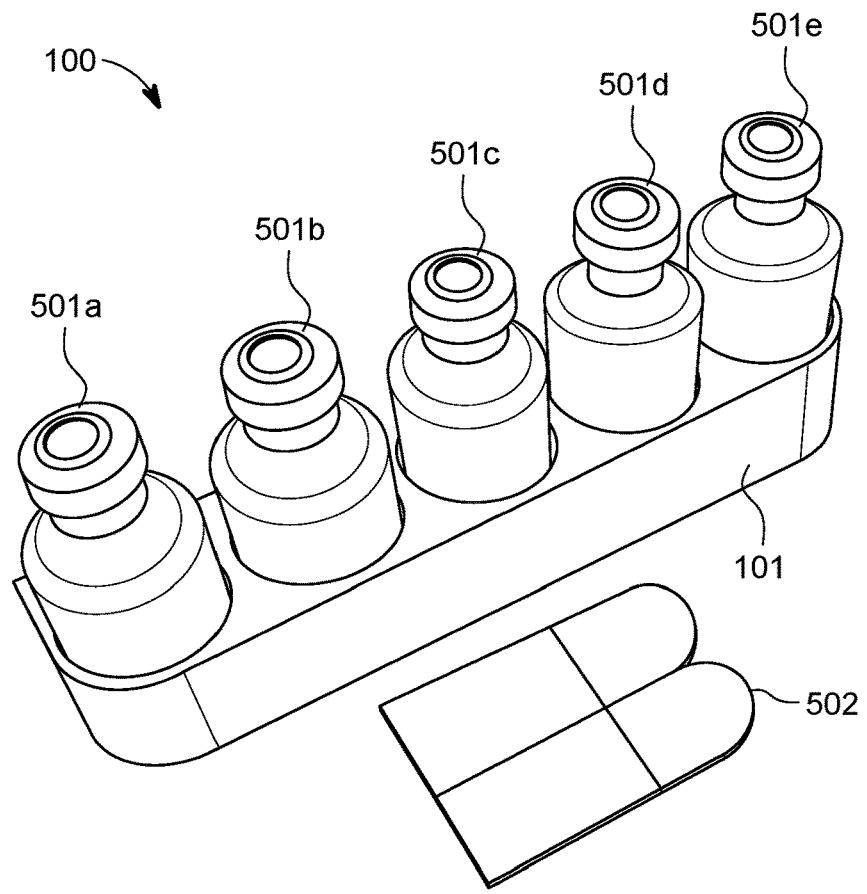
FIG. 5 illustrates an embodiment of an article of manufacture providing a wall-mounted insulin caddy holding insulin vials according to the present invention.

FIG. 5 illustrates an embodiment of an article of manufacture providing a wall-mounted insulin caddy holding insulin vials according to the present invention. A set of medicine vials 501a-e are shown in FIG. 5 being stowed within the storage locations 102a-e of the wall-mounted insulin caddy 100. The caddy body 101 is tall enough to cover the lower portion of each vial that contains the insulin while exposing enough of a top end of each vial to permit each one to be easily removed and replaced within the storage locations 102a-e as needed. A set of adhesive strips 502 is also shown In FIG. 5. The adhesive strips 502 are coupled to the flat rear surface 311 of the caddy body 101 to couple the wall-mounted insulin caddy 100 to a refrigerator wall 701 as shown in FIG. 7.

Figure 6:
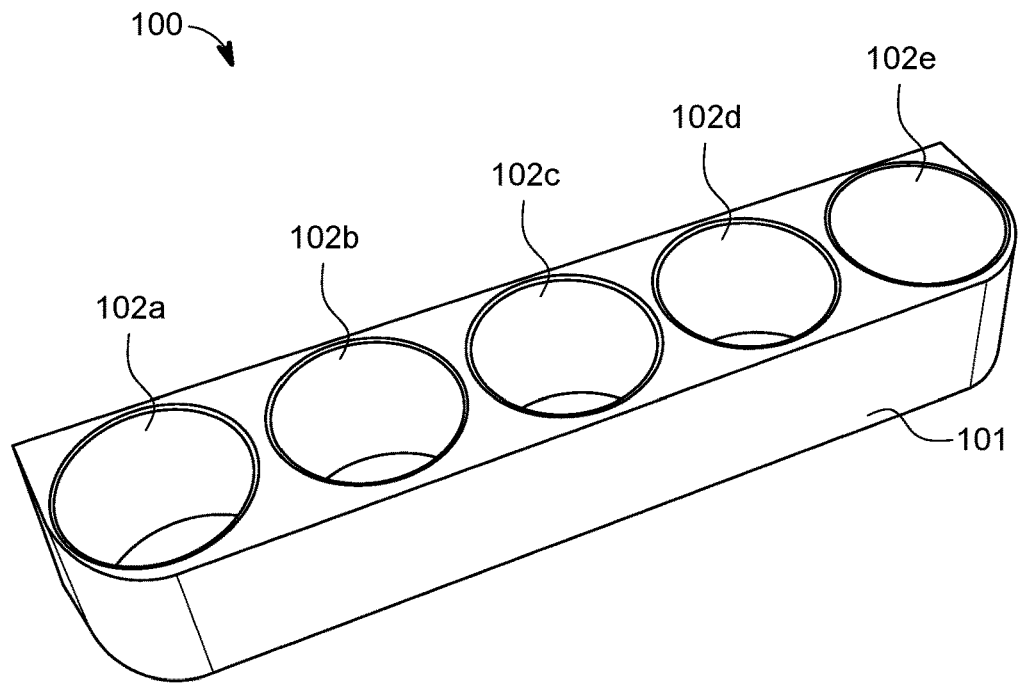
FIG. 6 illustrates an empty article of manufacture providing a wall-mounted insulin caddy according to the present invention.

FIG. 6 illustrates an empty article of manufacture providing a wall-mounted insulin caddy according to the present invention. Inner surfaces of each storage location 102a-e are shown. A label 601 may be included on an outside front surface 602 of the caddy body 101 to identify the contents of the vials 501a-e stored therein. This label 602 may be etched into the outside front surface 602 in a preferred embodiment, although other labeling mechanisms may also be utilized.

Figure 7:
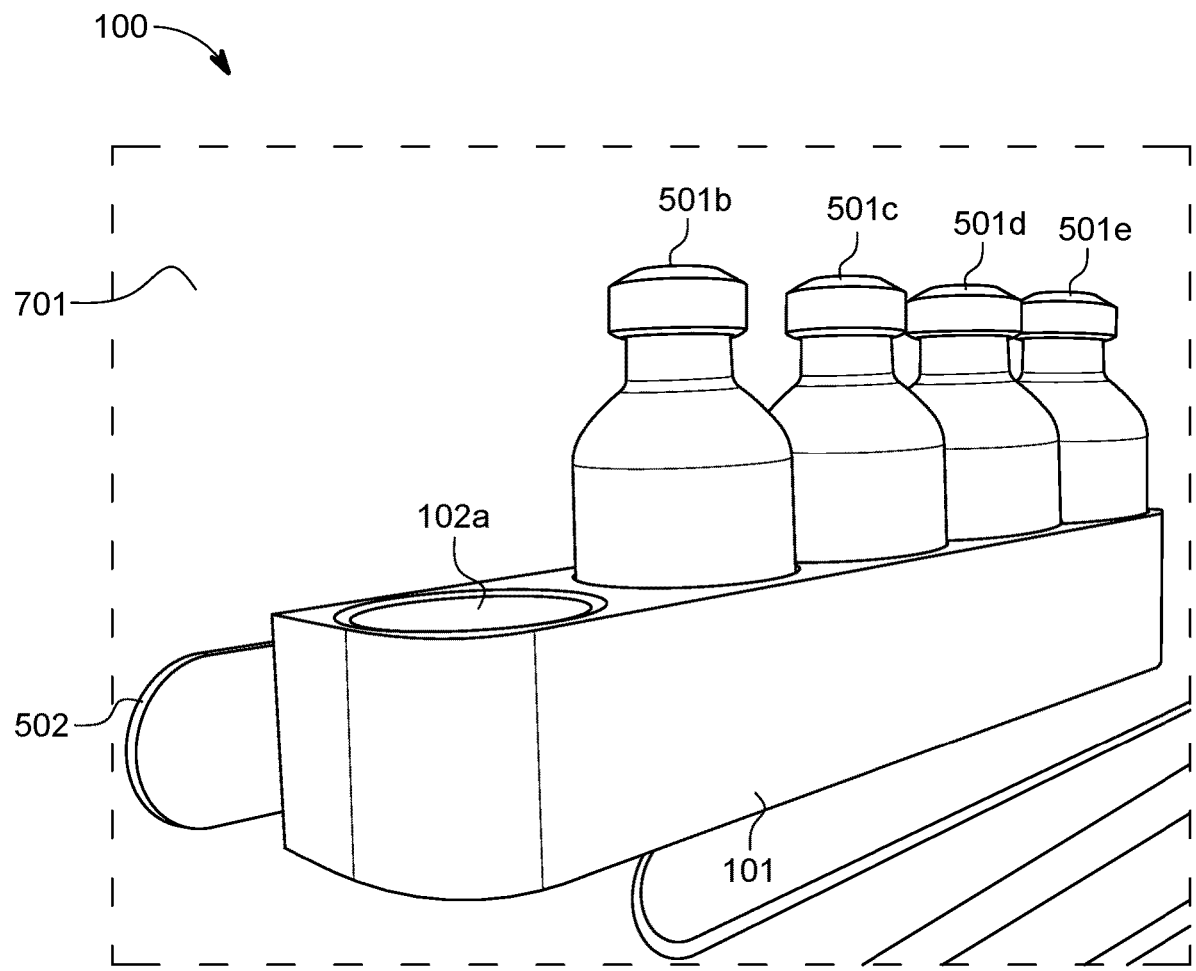
FIG. 7 illustrates an article of manufacture providing a wall-mounted insulin caddy installed within a refrigerated storage location according to the present invention.

FIG. 7 illustrates an article of manufacture providing a wall-mounted insulin caddy installed within a refrigerated storage location according to the present invention. The wall-mounted insulin caddy 100 is shown coupled to a refrigerator wall 701 with one or more adhesive strips 502 coupling the flat rear surface 311 of the caddy body 101 to the refrigerator wall 701. The adhesive strip 502 may be pulled to detach the wall-mounted insulin caddy 100 from the refrigerator wall 701 to move, clean, reposition, or remove the wall-mounted insulin caddy 100 as needed.

Even though particular combinations of features are recited in the present application, these combinations are not intended to limit the disclosure of the invention. In fact, many of these features may be combined in ways not specifically recited in this application. In other words, any of the features mentioned in this application may be included to this new invention in any combination or combinations to allow the functionality required for the desired operations.

No element, act, or instruction used in the present application should be construed as critical or essential to the invention unless explicitly described as such. Further, the phrase "based on" is intended to mean "based, at least in part, on" unless explicitly stated otherwise.

What is claimed is:

1. An article of manufacture providing a wall-mounted insulin caddy, the insulin caddy comprises:
   a caddy body having a flat rear surface, an outer front surface, a pair of rounded corners, a top caddy body surface, and a bottom caddy body surface, the caddy body comprises:
      a plurality of cylindrical storage locations, each of the plurality of cylindrical storage locations comprises a cavity within the caddy body accessible from a top caddy body surface for storing a vial; and
      a drainage hole from within the cylindrical storage locations through a bottom caddy surface; and one or more removable adhesive strips coupled to the flat rear surface for mounting the caddy body to a wall;

wherein the caddy body is made from a rigid plastic material comprising Polylactic Acid (PLA), Polyethylene terephthalate glycol (PET(G)), and Acrylonitrile, Butadiene, Styrene (ABS).

2. The insulin caddy according to claim 1, wherein the caddy body reduces external light passing into vials placed within one of the plurality of cylindrical storage locations.

3. The insulin caddy according to claim 1, wherein the caddy body further comprises a label on the outer front surface for identifying contents of any vials stored within the caddy body.

4. The insulin caddy according to claim 1, wherein the plurality of cylindrical storage locations comprises multiple storage locations.

5. The insulin caddy according to claim 4, wherein the plurality of cylindrical storage locations has identically sized cylindrical cavities.

6. The insulin caddy according to claim 4, wherein each of the plurality of cylindrical storage locations has a chamfered vial slot opening for easier vial installation.

7. A wall-mounted insulin caddy comprising:
a caddy body having a flat rear surface, an outer front surface, and a pair of rounded corners, the caddy body comprises:
 a plurality of cylindrical storage locations, each of the plurality of cylindrical storage locations comprises a cavity within the caddy body accessible from a top caddy body surface for storing a vial; and
 a drainage hole from within the cylindrical storage locations through a bottom caddy surface;
one or more removable adhesive strips coupled to the flat rear surface for mounting the caddy body to a wall; and
the label on the outer front surface for identifying contents of any vials stored within the caddy body;
wherein the caddy body reduces external light passing into vials placed within one of the plurality of cylindrical storage locations;
wherein each of the plurality of cylindrical storage locations has a chamfered vial slot opening for easier vial installation; and
wherein the caddy body is made from a rigid plastic material comprising Polylactic Acid (PLA), Polyethylene terephthalate glycol (PET(G)), and Acrylonitrile, Butadiene, Styrene (ABS).

\* \* \* \* \*